US005476987A

United States Patent [19]

Kitamura et al.

[11] Patent Number: 5,476,987

[45] Date of Patent: Dec. 19, 1995

[54] METHOD OF REMOVING HALOGENATED AROMATIC COMPOUND FROM HYDROCARBON OIL

[75] Inventors: Shuji Kitamura, Kyoto; Tsuneo Yano, Saitama; Humio Tanimoto, Kyoto, all of Japan

[73] Assignees: Research Institute For Production Development, Kyoto; Mitsui & Co., Ltd., Tokyo, both of Japan

[21] Appl. No.: 190,084

[22] PCT Filed: Jan. 11, 1993

[86] PCT No.: PCT/JP93/00036

§ 371 Date: Apr. 29, 1994

§ 102(e) Date: Apr. 29, 1994

[87] PCT Pub. No.: WO93/25635

PCT Pub. Date: Dec. 23, 1993

[30] Foreign Application Priority Data

Jun. 5, 1992 [JP] Japan .................................... 4-188564

[51] Int. Cl.$^6$ .............................. C07C 7/00; C10G 17/00

[52] U.S. Cl. .......................... 585/853; 585/854; 585/857; 585/860; 585/866; 208/262.1; 208/262.5

[58] Field of Search .................................... 585/853, 854, 585/857, 860, 866; 208/262.1, 262.5

[56] References Cited

U.S. PATENT DOCUMENTS

| | | | |
|---|---|---|---|
| 2,951,804 | 9/1960 | Juliard . | |
| 4,327,027 | 4/1982 | Howard et al. . | |
| 4,327,027 | 4/1982 | Howard et al. | 260/340.3 |
| 4,532,028 | 7/1985 | Peterson | 208/262 |

FOREIGN PATENT DOCUMENTS

| | | |
|---|---|---|
| 1181771 | 1/1985 | Canada . |
| 1206508 | 7/1983 | Italy . |
| 61-500442 | 3/1986 | Japan . |
| 3-90173 | 4/1991 | Japan . |

*Primary Examiner*—Asok Pal
*Assistant Examiner*—Nhat D. Phan
*Attorney, Agent, or Firm*—Burns, Doane, Swecker & Mathis

[57] ABSTRACT

A safe and reliable method of removing halogenated aromatic compounds present in small amounts in hydrocarbon oil constituted mainly by non-aromatic hydrocarbon oil. The hydrocarbon oil is contacted with a heat-resistant alkaline polar solvent in the presence of an alkaline at a temperature ranging from about 100° C. to 300° C., and the non-aromatic hydrocarbon oil and heat-resistant alkaline polar solvent are then separated, thereby removing the halogenated aromatic compounds from the hydrocarbon oil.

22 Claims, No Drawings

METHOD OF REMOVING HALOGENATED AROMATIC COMPOUND FROM HYDROCARBON OIL

BACKGROUND OF THE INVENTION

1. Field of the Invention

The present invention relates to a safe method for removing halogenated aromatic compounds from hydrocarbon oil contaminated by halogenated aromatic compounds such as polychlorinated biphenyl (hereinafter "PCB"), using chemical reaction processing and extraction.

2. Description of Related Art

It is known that it is extremely difficult to treat hydrocarbon oil that during use has become contaminated by PCB or other such halogenated aromatic compound. This has led to considerable efforts directed toward the removal or decompsition of halogenated aromatic compounds. Methods for accomplishing this using a reaction process that takes place in the presence of an alkali include the alumina-alkali process disclosed by U.S. Pat. No. 2,951,804. U.S. Pat. No. 4,532,028 discloses a method of reacting alkali and a PCB content of up to 50,000 ppm in a mixture of alkyl or alkylene sulfoxide and polyole, thereby reducing the content to several ppm. Other examples include Canadian Patent No. 1,181,771 which discloses a method employing melted sodium, and Italian Patent No. 1,206,508 which discloses a method using alkaline earth metal on which PEG is adsorbed.

Each method has its good points and, in the case of non-aromatic hydrocarbon and other such samples containing high concentrations of halogenated aromatic compounds are recognized as being effective techniques for reducing concentrations of halogenated aromatic compounds to a low level.

However, with the prior art techniques it is not possible to further remove halogenated aromatic compounds from samples having a low concentration thereof, so that the halogenated aromatic compound content is further reduced to the extent that the inclusion thereof is substantially not recognizable; it is not yet possible to reduce the halogenated aromatic compound concentration to 1 ppm or below. Moreover, processes that are specifically for extracting contaminants having low concentration levels are considered very difficult. Also, it is widely known that heating the extraction solvent used in the prior art methods to a high temperature of 120° C. or over in the presence of an alkali or alkali metal has a chemically destablizing effect that promotes solvent decomposition and polymerization, degrading the basic function of the extraction solvent.

SUMMARY

The inventor of the present invention investigated various ways of eliminating such drawbacks and discovered a highly effective method of removing aromatic compounds from non-aromatic hydrocarbon oil. In accordance with the method, a heat-resistant alkaline polar solvent that has low compatibility with non-aromatic hydrocarbon oil, a high boiling point and good high-temperature stability with respect to alkalis is contacted with non-aromatic hydrocarbon oil containing a small amount of an aromatic compound, in the presence of an alkali and at a temperature ranging from about 100° C. to about 300° C.

Thus, in the method of the present invention for removing halogenated aromatic compounds from hydrocarbon oil which is constituted mainly of non-aromatic hydrocarbon oil and contains a small amount of halogenated aromatic compound, the non-aromatic hydrocarbon oil is contacted with a heat-resistant alkaline polar solvent, and the non-aromatic hydrocarbon oil and heat-resistant alkaline polar solvent are then separated.

Hence, the halogenated aromatic compound is PCB and analogous compounds thereof. Substances that may be used to constitute the heat-resistant alkaline polar solvent include 1, 3-dimethyl-2-imidazolidinone, sulfolane, ethylene glycol, diethylene glycol, triethylen glycol, polyethylene glycol, low alkyl-ethers of polyethylene glycol, trimethylene glycol, butylene glycol, and low alkyl-ethers thereof.

Industrially these heat-resistant alkaline polar solvents are used relatively extensively and have low toxicity and risk. What should be noted is their outstanding ability to extract halogenated aromatic compounds. However, if only an extraction process is used, the removal effect when the aromatic compounds are present in small quantities in the order of parts per million. It was found that when an alkali was used with the aim of improving the removal effect and substantially eliminating halogenated aromatic compounds, the interaction between heat-resistant alkaline polar solvents and halogenated aromatic compounds was rapid and pronounced, and at high temperatures the effect was greater than expected.

There were found to be slight differences in the halogenated aromatic compound removal effect of the various heat-resistant alkaline polar solvents. It was confirmed that 1, 3-dimethyl-2-imizazolidinone (herein after "DMI"), sulfolane, and also a mixture of 1, 3-dimethyl-2-imidazolidinone and sulfolane, are heat-resistant alkaline polar solvents that are effective under all of the conditions.

Depending on the purpose, ethylene glycol, diethylene glycol, triethylene glycol, polyethylene glycol, low alkyl-ethers of polyethylene glycol, trimethylene glycol, butylene glycol and low alkyl-ethers thereof are also effective. When the aim is to remove halogenated aromatic compounds with high efficiency, it is preferable to use these solvents in an auxiliary role to make it easier to handle DMI or sulfolane.

While some effect is obtained even when non-aromatic hydrocarbon oil and heat-resistant alkaline polar solvent are contacted at a temperature of 100° C. or below, such a temperature will not produce a strong effect. On the other hand, although stable the heat-resistant alkaline polar solvent is an organic solvent and, as such, will gradually be degraded by a contact temperature of 300° C. or above. Therefore, preferably a contact temperature is used that is in the approximate range of from 100° C. to 300° C. for contact between the non-aromatic hydrocarbon oil and the heat-resistant alkaline polar solvent, and more preferably within the range of from 150° C. to 250° C.

Another factor involved in improving the efficiency with which aromatic compounds are removed is the method used for contacting the non-aromatic hydrocarbon oil with the heat-resistant alkaline polar solvent. The contact process can be effected using a reaction vessel and a stirrer, or a packed column and a circulation system, for example. The reaction efficiency can be improved by providing the packed column with an absorption layer in addition to the packing.

The final step in the method of removing halogenated aromatic compounds from non-aromatic hydrocarbon oil in accordance with the present invention involves the separation of the processed non-aromatic hydrocarbon oil and heat-resistant alkaline polar solvent. After separation it is preferable to recycle the heat-resistant alkaline polar solvent which contains alkaline and reaction products.

It is not easy to clarify how the structure of a halogenated aromatic compound thus removed has changed, as this will differ depending on the initial structure of the halogenated aromatic compound. Based on chemical commonsense it could be that chlorine substitutes for a hydroxyl group or bonds with alkyl-ether, but in either case it is important that chlorine be dissociated from the initial structure of the aromatic compound. In this invention, therefore, an alkali selected from the group caustic soda, caustic potash, sodium alcohol ate, potassium alcoholate, and calcium hydroxide, may be used, preferably in a ratio of not less than 1.0 times the calculated halogen content of the non-aromatic hydrocarbon oil.

As used here, non-aromatic hydrocarbon oil refers to an oil having a high boiling point and good thermal stability, such as electrical insulating oil, industrial lubricating oil, and heat transfer oil.

DETAILED DESCRIPTION OF THE PREFERRED EMBODIMENTS

EXAMPLE 1

As listed in Table 1, a sample consisting of 50 g of reclaimed transformer oil containing 40 mg/l of PCB was mixed with 25 g of DMI and 5 g of sodium ethoxide (NaOEt, in Table 1) in a 100 ml flask, and the mixture was then stirred briskly while being maintained at a temperature of 160° C. for about 2 hours. After cooling the mixture to room temperature, the lower layer of DMI was removed and the PCB in the oil layer was analyzed by gas chromatography in accordance with the method specified by JIS (Japanese Industrial Standard) K0093, and it was confirmed that the PCB content had decreased to 1.2 mg/l.

EXAMPLE 2

As listed in Table 1, a sample consisting of 40 g of reclaimed transformer oil containing 40 mg/l of PCB was mixed with 25 g of suflolane, 0.5 g of β-cyclodextrin and 0.5 g of sodium ethoxide in a flask, and the mixture was then stirred briskly while being maintained at a temperature of 200° C. for about 2 hours. After cooling the mixture to room temperature, the layer of sulfolane was removed and the PCB in the layer was analyzed, whereby it was confirmed that the PCB content had decreased to 2.9 mg/l.

EXAMPLE 3

As listed in Table 1 , a sample consisting of 50 g of reclaimed transformer oil containing 15 mg/l of PCB was mixed with 25 g of sulfolane and 1.5 g of caustic soda (NaOH in Table 1) in a flask, and the mixture was then stirred briskly while being maintained at a temperature of 200° C. for about 2 hours. After cooling the mixture to room temperature, the lower layer of sulfolane was removed and the PCB in the oil layer was analyzed, whereby it was confirmed that PCB content had decreased to 0.61 mg/l.

EXAMPLE 4

As listed in Table 1, a sample consisting of 50 g of reclaimed transformer oil containing 15 mg/l of PCB was mixed with 25 g of suflolane and 5 g of caustic soda in a flask, and the mixture was then stirred briskly while being maintained at a temperature of 160° C. for about 2.5 hours. After cooling the mixture to room temperature, the lower layer of sulfolane was removed and the PCB in the oil layer was analyzed, whereby it was confirmed that the PCB content had decreased to 1.9 mg/l.

EXAMPLE 5

As listed in Table 1, a sample consisting of 100 g of reclaimed transformer oil containing 40 mg/l of PCB was mixed with 50 g of sulfolane and 2 g of sodium ethoxide in a flask, and the mixture was then stirred briskly while being maintained at a temperature of 200° C. for about 2 hours. After cooling the mixture to room temperature, the lower layer of sulfolane was removed and the PCB in the oil layer was analyzed, whereby it was confirmed that the PCB content had decreased to the PCB detection limit of 0.5 mg/l or less.

EXAMPLE 6

As listed in Table 1, a sample consisting of 100 g of reclaimed transformer oil containing 40 mg/l of PCB was mixed with 50 g of sulfolane and 3 g of caustic soda in a flask, and the mixture was then stirred briskly while being maintained at a temperature of 160° C. for about 2 hours. After cooling the mixture to room temperature, the lower layer of sulfolane was removed and the PCB in the oil layer was analyzed, whereby it was confirmed that the PCB content had decreased to 0.5 mg/l or less.

EXAMPLE 7

As listed in Table 1, a sample consisting of 50 g of reclaimed transformer oil containing 40 mg/l of PCB was mixed with 5 g of sulfolane and 1.5 g of sodium ethoxide in a flask, and the mixture was then stirred briskly while being maintained at a temperature of 200° C. for about 2 hours. After cooling the mixture to room temperature, the lower layer of sulfolane was removed and the PCB in the oil layer was analyzed, whereby it was confirmed that the PCB content had decreased to 0.5 mg/l or less.

EXAMPLE 8

As listed in Table 1, a sample consisting of 50 g of reclaimed transformer oil containing 12 mg/l of PCB was mixed in a flask with 25 g of a mixed solvent consisting of 12.5 g of diethylene glycol (hereinafter "DEG") and 12.5 g of DMI, and 0.1 g of caustic soda, and the mixture was then stirred briskly while being maintained at a temperature of from 180° C. to 200° C. for about 2 hours. After cooling the mixture to room temperature, the lower layer of DEG and DMI was removed and the PCB in the oil layer was analyzed, whereby it was confirmed that the PCB content had decreased to the PCB detection limit of 0.5 mg/l or less.

EXAMPLE 9

As listed in Table 1, a sample consisting of 50 g of reclaimed transformer oil containing 12 mg/l of PCB was mixed in a flask with 25 g of a mixed solvent consisting of 1.25 g Of polyethylene glycol (hereinafter "PEG") having a mean molecular weight of 200 and 23.75 g of DMI, and 0.1 g of caustic soda, and the mixture was then stirred briskly while being maintained at a temperature of from 180° C. to 200° C. for about 2 hours. After cooling the mixture to room temperature, the lower layer of PEG and DMI was removed and the PCB in the oil layer was analyzed, whereby it was confirmed that the PCB content had decreased to the PCB detection limit of 0.5 mg/l or less.

EXAMPLE 10

As listed in Table 1, a sample consisting of 50 g of reclaimed transformer oil containing 12 mg/l of PCB was mixed in a flask with 25.5 g of a mixed solvent consisting of 0.5 g of 18-crown-6 and 25 g of DMI, and 0.1 g of caustic potash (KOH in Table 1), and the mixture was then stirred briskly while being maintained at a temperature of from 170° C. to 180° C. for about 2 hours. After cooling the mixture to room temperature, the lower layer of 18-crown-5 and DMI was removed and the PCB in the oil layer was analyzed, whereby it was confirmed that the PCB content had decreased to the PCB detection limit of 0.5 mg/l or less.

EXAMPLE 11

As listed in Table 1, a sample consisting of 50 g of reclaimed transformer oil containing 12 mg/l of PCB was mixed in a flask with 25 g of DMI and 0.05 g of caustic soda, and the mixture was then stirred briskly while being maintained at a temperature of from 200° C. to 210° C. for about 2 hours. After cooling the mixture to room temperature, the lower layer of DMI was removed and the PCB in the oil layer was analyzed, whereby it was confirmed that the PCB content had decreased to the PCB detection limit of 0.5 mg/l or less.

EXAMPLE 12

As listed in Table 1, a sample consisting of 50 g of reclaimed transformer oil containing 12 mg/l of PCB was mixed in a flask with 25 g of sulfolane and 0.05 g of caustic soda, and the mixture was then stirred briskly while being maintained at a temperature of from 195° C. to 205° C. for about 2 hours. After cooling the mixture to room temperature, the lower layer of sulfolane was removed and the PCB in the oil layer was analyzed, whereby it was confirmed that the PCB content had decreased to the PCB detection limit of 0.5 mg/l or less.

COMPARATIVE EXAMPLE 1

As listed in Table 1, a sample consisting of 200 g of reclaimed transformer oil containing 50 mg/l of PCB was mixed in a flask with 50 g of DMI, and the mixture was then stirred briskly while being maintained at a temperature of 80° C. for about 1 hour. After cooling the mixture to room temperature, the lower layer of DMI was removed. On analyzing the PCB in the oil layer, the PCB content was found to be 40 mg/l.

COMPARATIVE EXAMPLE 2

As listed in Table 1, a sample consisting of 100 g of reclaimed transformer oil containing 50 mg/l of PCB was mixed in a flask with 50 g of DMI and 0.5 g of caustic soda, and the mixture was then stirred briskly while being maintained at a temperature of 80° C. for about 1 hour. After cooling the mixture to room temperature, the lower layer of DMI was removed. On analyzing the PCB in the oil layer, the PCB content was found to be 48 mg/l.

COMPARATIVE EXAMPLE 3

As listed in Table 1, a sample consisting of 100 g of reclaimed transformer oil containing 100 mg/l of PCB was mixed in a flask with 72.5 g of DMI and 0.45 g of sodium ethoxide, and the mixture was then stirred briskly while being maintained at a temperature of 80° C. for about 1 hour. After cooling the mixture to room temperature, the lower layer of DMI was removed. On analyzing the PCB in the oil layer, the PCB content was found to be 31 mg/l.

COMPARATIVE EXAMPLE 4

As listed in Table 1, a sample consisting of 100 g of reclaimed transformer oil containing 100 mg/l of PCB was mixed in a flask was subjected to 0.5 hours of ultrasonic agitation at room temperature. Analysis showed that the PCB content was 59 mg/l.

COMPARATIVE EXAMPLE 5

As listed in Table 1, a sample consisting of 50 g of reclaimed transformer oil containing 40 mg/l of PCB was mixed in a flask with 25 g of DMI and 0.5 g of β-cyclodextrin, and the mixture was then stirred briskly while being maintained at a temperature of 200° C. for about 2 hours. After cooling the mixture to room temperature, the lower layer of DMI was removed. On analyzing the PCB in the oil layer, the PCB content was found to be 12 mg/l.

Thus, in each of the inventive examples PCB was removed with good efficiency. However, even using the same conditions the addition of β-cyclodextrin tended somewhat to hinder PCB removal. In both inventive and comparative examples, in accordance with the procedure of JIS K0093 analysis of the PCB was done by gas chromatography.

TABLE 1-1

| Conditions | Sample Reclaimed transformer oil (g) | Sample PCB (mg/l) | Extraction agent (g) | Alkali (catalyst) (g) | Processing temperature (°C.) | Processing time (Hr) | Remaining PCB content (mg/l) |
|---|---|---|---|---|---|---|---|
| Inventive examples | | | | | | | |
| 1 | 50 | 40 | DMI 25 | NaOEt 0.5 | 160 | 2 | 1.2 |
| 2 | 50 | 40 | Sulfolane 25 | β-cyclodextrin 0.5<br>NaOEt 0.5 | 200 | 2 | 2.9 |
| 3 | 50 | 15 | Sulfolane 25 | NaOH beads 1.5 | 200 | 2 | 0.61 |
| 4 | 50 | 15 | Sulfolane 25 | NaOH beads 1.5 | 160 | 2.5 | 1.9 |
| 5 | 100 | 40 | Sulfolane 50 | NaOEt 2 | 200 | 2 | 0.5 or less |

TABLE 1-2

| Conditions | Sample Reclaimed transformer oil (g) | Sample PCB (mg/l) | Extraction agent (g) | Alkali (catalyst) (g) | Processing temperature (°C.) | Processing time (Hr) | Remaining PCB content (mg/l) |
|---|---|---|---|---|---|---|---|
| Inventive examples | | | | | | | |
| 6 | 100 | 40 | Sulfolane 50 | NaOH 3 beads | 160 | 2 | 0.5 or less |
| 7 | 50 | 40 | Sulfolane 5 | NaOEt 1.5 | 200 | 2 | 0.5 or less |
| 8 | 50 | 12 | DEG 12.5 DMI 12.5 | NaOH 0.1 | 180–200 | 2 | 0.5 or less |
| 9 | 50 | 12 | PEG (200) 1.25 DMI 23.75 | NaOH 0.1 | 180–200 | 2 | 0.5 or less |
| 10 | 50 | 12 | 18-crown-6 0.5 DMI 25 | KOH 0.1 | 170–180 | 2 | 0.5 or less |

TABLE I-3

| Conditions | Sample Reclaimed transformer oil (g) | Sample PCB (mg/l) | Extraction agent (g) | Alkali (catalyst) (g) | Processing temperature (°C.) | Processing time (Hr) | Remaining PCB content (mg/l) |
|---|---|---|---|---|---|---|---|
| Inventive examples | | | | | | | |
| 11 | 50 | 12 | DMI 25 | NaOH 0.05 | 200–210 | 2 | 0.5 or less |
| 12 | 50 | 12 | Sulfolane 25 | NaOH 0.05 | 195–205 | 2 | 0.5 or less |
| Comparative examples | | | | | | | |
| 1 | 200 | 50 | DMI 50 | None | 80 | 1 | 40 |
| 2 | 100 | 50 | DMI 25 | NaOH 0.5 | 80 | 1 | 48 |
| 3 | 50 | 100 | DMI 72.5 | NaOEt 0.45 | 80 | 1 | 31 |
| 4 | 100 | 100 | None | None; ultrasonic waves at room temperature | | 0.5 | 59 |
| 5 | 50 | 40 | DMI 25 | β-cyclo- 0.5 dextrin | 200 | 2 | 12 |

Industrial Applicability

As described in the foregoing, in accordance with the present invention, PCB and other such halogenated aromatic compounds which, even in small quantities, pose environmental problems and are directly hazardous to the human body, can be removed from hydrocarbon oil having non-aromatic hydrocarbon oil as the main constituent, to the extent that the PCB or other such compound is rendered substantially harmless.

We claim:

1. A method of removing halogenated aromatic compounds from hydrocarbon oil, comprising:

contacting hydrocarbon oil that includes non-aromatic hydrocarbon oil and contains a halogenated aromatic compound with a heat-resistant alkaline polar solvent in the presence of an alkali, and then separating the non-aromatic hydrocarbon oil and the heat-resistant alkaline polar solvent;

in which the heat-resistant alkaline polar solvent is an organic solvent constituted by a mixture of 1, 3-dimethyl- 2-imidazolidinone and sulfolane.

2. The method according to claim 1, in which the halogenated aromatic compound is polychlorinated biphenyl.

3. The method according to claim 1, in which the alkali is constituted by one or more selected from a group consisting of caustic soda, caustic potash, sodium alcoholate, potassium alcoholate, and calcium hydroxide.

4. The method according to claim 3, in which the one or more alkalis are used in a ratio that is not less than 1.0 times the calculated halogen content of the non-aromatic hydrocarbon oil.

5. The method according to claim 1, in which the heat resistant alkaline polar solvent is a mixture of an organic solvent constituted by 1, 3-dimethyl- 2-imidazolidinone and sulfolane, and one or more organic solvents selected from a group consisting of ethylene glycol, diethylene glycol, triethylene glycol, polyethylene glycol, and alkyl-ethers thereof, trimethylene glycol, butylene glycol, and alkyl-ethers thereof.

6. The method according to claim 1, in which the non-aromatic hydrocarbon oil and the heat-resistant alkaline polar solvent are contacted at a temperature of from about 100° C. to about 300° C.

7. The method according to claim 1, in which the non-aromatic hydrocarbon oil and the heat-resistant alkaline polar solvent are contacted at a temperature of from about 150° C. to about 250° C.

8. The method according to claim 1, wherein the non-aromatic oil is selected from a group consisting of electrical insulating oil, industrial lubricating oil, and heat transfer oil.

9. A method of removing halogenated aromatic compounds from hydrocarbon oil, comprising:

contacting hydrocarbon oil that includes non-aromatic hydrocarbon oil and contains a halogenated aromatic compound with a heat-resistant alkaline polar solvent in the presence of an alkali; and then separating the non-aromatic hydrocarbon oil and the heat-resistant alkaline polar solvent;

in which the heat-resistant alkaline polar solvent is an organic solvent constituted by 1,3-dimethyl -2-imadazolidinone.

10. The method according to claim 1, in which the heat-resistant alkaline polar solvent is a mixture of an organic solvent constituted by 1, 3-dimethyl- 2-imidazolidinone, and one or more organic solvents selected from a group consisting of ethylene glycol, diethylene glycol, triethylene glycol, polyethylene glycol, and alkyl-ethers thereof, trimethylene glycol, butylene glycol, and alkyl-ethers thereof.

11. The method according to claim 9, in which the non-aromatic hydrocarbon oil and the heat-resistant alkaline polar solvent are contacted at a temperature of from about 100° C. to about 300° C.

12. The method according to claim 9, in which the non-aromatic hydrocarbon oil and the heat-resistant alkaline polar solvent are contacted at a temperature of from about 150° C. to about 250° C.

13. The method according to claim 9, in which the halogenated aromatic compound is polychlorinated biphenyl.

14. The method according to claim 19, in which the alkali is constituted by one or more selected from a group consisting of caustic soda, caustic potash, sodium alcoholate, potassium alcoholate, and calcium hydroxide.

15. The method according to claim 14, in which the one or more alkalis are used in a ratio that is not less than 1.0 times the calculated halogen content of the non-aromatic hydrocarbon oil.

16. A method of removing halogenated aromatic compounds from hydrocarbon oil, comprising:

contacting hydrocarbon oil that includes non-aromatic hydrocarbon oil and contains a halogenated aromatic compound with a heat-resistant alkaline polar solvent in the presence of an alkali; and then separating the non-aromatic hydrocarbon oil and the heat-resistant alkaline polar solvent;

in which the heat-resistant alkaline polar solvent is an organic solvent constituted by sulfolane.

17. The method according to claim 16, in which the heat-resistant alkaline polar solvent is a mixture of an organic solvent constituted by sulfolane, and one or more organic solvents selected from a group consisting of ethylene glycol, diethylene glycol, triethylene glycol, polyethylene glycol, and alkyl-ethers thereof, trimethylene glycol, butylene glycol, and alkyl-ethers thereof.

18. The method according to claim 16, in which the non-aromatic hydrocarbon oil and the heat-resistant alkaline polar solvent are contacted at a temperature of from about 100° C. to about 300° C.

19. The method according to claim 16, in which the non-aromatic hydrocarbon oil and the heat-resistant alkaline polar solvent are contacted at a temperature of from about 150° C. to about 250° C.

20. The method according to claim 16, in which the halogenated aromatic compound is polychlorinated biphenyl.

21. The method according to claim 16, in which the alkali is constituted by one or more selected from a group consisting of caustic soda, caustic potash, sodium alcoholate, potassium alcoholate, and calcium hydroxide.

22. The method according to claim 21, in which the one or more alkalis are used in a ratio that is not less than 1.0 times the calculated halogen content of the non-aromatic hydrocarbon oil.

* * * * *